US00PP09178P

United States Patent [19]

Ogilvie

[11] Patent Number: Plant 9,178

[45] Date of Patent: Jun. 27, 1995

[54] SHRUB ROSE PLANT NAMED 'SIMON FRASER'

[75] Inventor: Ian S. Ogilvie, L'Assomption, Canada

[73] Assignee: Her Majesty the Queen in right of Canada, as represented by the Minister of Agriculture, Ottawa, Canada

[21] Appl. No.: 207,028

[22] Filed: Mar. 7, 1994

[51] Int. Cl.[6] ..... A01H 5/00

[52] U.S. Cl. ..... Plt./1

[58] Field of Search ..... Plt. 1, 22, 26, 27

[56] References Cited

PUBLICATIONS

Ogilvie, et al., 1993, "Simon Fraser Rose", Hortscience 28(6):680.

*Primary Examiner*—Howard J. Locker

*Attorney, Agent, or Firm*—Burns, Doane, Swecker & Mathis

[57] ABSTRACT

A new and distinct variety of shrub rose plant is provided which forms attractive light pink blossoms that commonly are borne in clusters and which at least initially are single. The new variety exhibits an upright growth habit with glossy foliage, and good winter hardiness. The new variety propagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination during 1986 at the Central Experimental Farm, Ottawa, Ontario, Canada. The female parent (i.e., the seed parent) was [Bonanza×)Arthur Bell×(Red Dawn×Suzanne)], and the male parent (i.e., the pollen parent) was [(*Rosa kordesii*) open pollinated×(*Rosa kordesii*) open pollinated×Champlain)]. Each of the named plants utilized in the breeding program was non-patented in the United States. Selective study carried out at L'Assomption, Quebec, Canada, resulted in the identification of a single plant of the new variety.

It was found that the new variety of shrub rose plant of the present invention prossesses the following combination of characteristics:

(a) exhibits an upright growth habit with glossy foliage,
(b) forms in clusters attractive pink blossoms that at least initially are single,
(c) propagates well by the use of softwood cuttings,
(d) exhibits a good winter hardiness, and
(e) is particularly well suited for growing in the landscape.

The rose plants can be grown well on their own roots out-of-doors without protection at L'Assomption, Quebec, Canada. Blossoms commonly appear from June to early October. The first bloom commonly appears as a heavy flush, and the blossoming commonly repeats thereafter in a somewhat diminished profusion. It is found that older plants flower better than extremely young plants as would be expected.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogenous and stable and have been shown to be strictly transmissible by asexual propagation by the rooting of softwood stem cuttings and by tissue culture conducted at L'Assomption, Quebec, Canada.

The new variety has been named the Simon Fraser variety.

BRIEF DESCRIPTION OF THE PHOTOGRAPHS

The accompanying photographs show, as nearly true as it is reasonably possible to make the same in color illustrations of this character, typical specimens of plants and plant parts of the new variety. The rose plants of the new variety described herein were approximately 5 to 6 years of age and were photographed during September 1993 while growing on their own roots at L'Assomption, Quebec, Canada.

FIG. 1 illustrates a group of open flowers and foliage of the new variety while growing in the landscape, FIG. 2 illustrates an open flower and buds of the new variety with foliage in the background while growing in the landscape, FIG. 3 illustrates a specimen of a young bud of the new variety wherein the sepals are open and the petals are beginning to open, FIG. 4 illustrates a specimen of a young flower of the new variety wherein the petals are in a slightly more advanced stage of opening, FIG. 5 illustrates a specimen of a young flower of the new variety as the petals assume a further stage of opening, FIG. 6 illustrates a specimen of a flower of the new variety at a more advanced stage of opening than as illustrated in FIG. 5, FIG. 7 illustrates a specimen of a flower of the new variety at a more advanced stage of opening than as illustrated in FIG. 6, FIG. 8 illustrates on the left a specimen of a floral receptacle showing the arrangement of the stamens (sepals removed), and on the right a specimen of a floral receptacle showing the arrangement of the pistils (sepals and stamens removed), FIG. 9 illustrates a specimen of new growth of the new variety, FIG. 10 illustrates the upper surfaces of typical leaves of the new variety with a specimen having five leaflets being shown on the left and a specimen having three leaflets being shown on the right, and FIG. 11 illustrates the under surfaces of typical leaves of the new variety with a specimen having five leaflets being shown on the left and a specimen having three leaflets being shown on the right.

DETAILED DESCRIPTION

Figure 1:
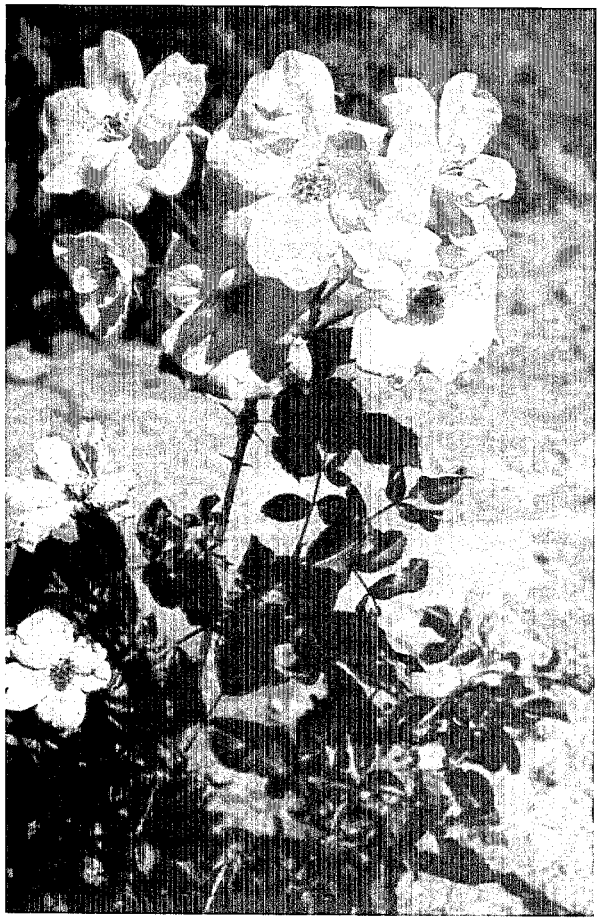
Figure 2:
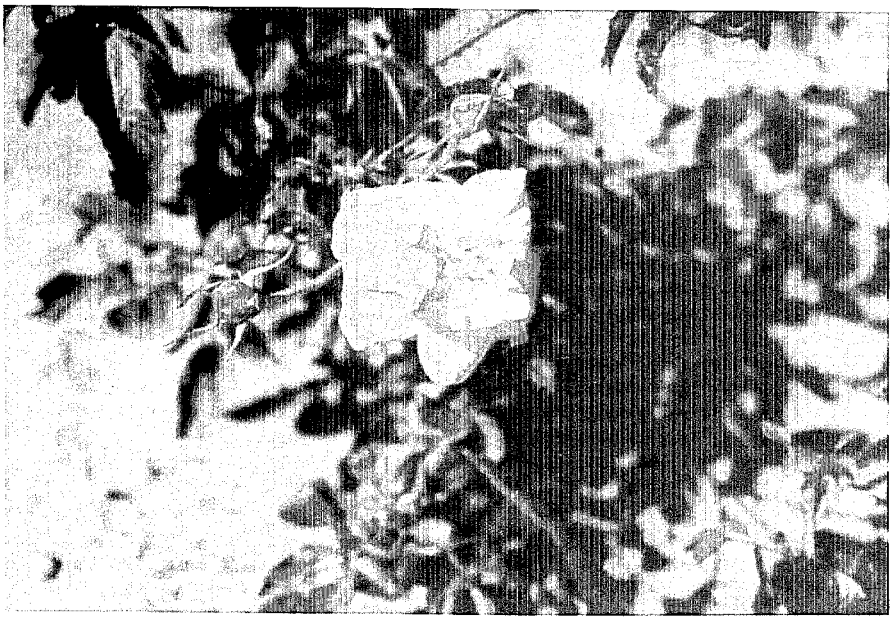
Figure 3:
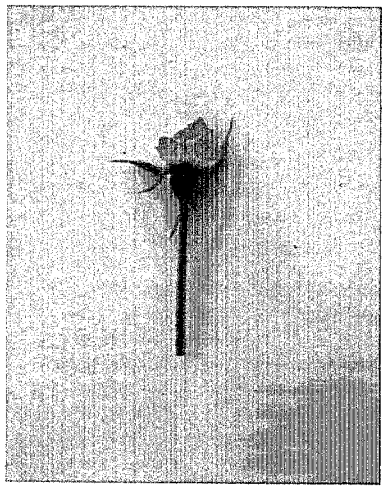
Figure 4:
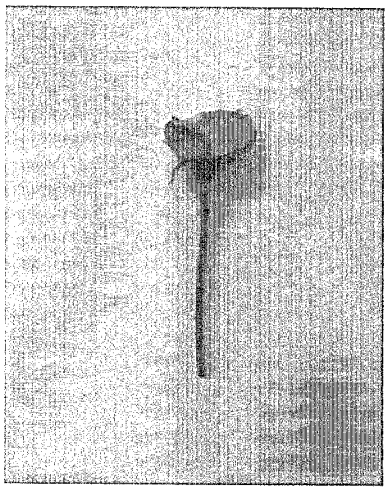
Figure 5:
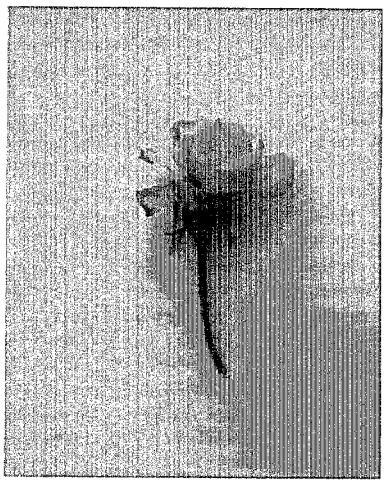
Figure 6:
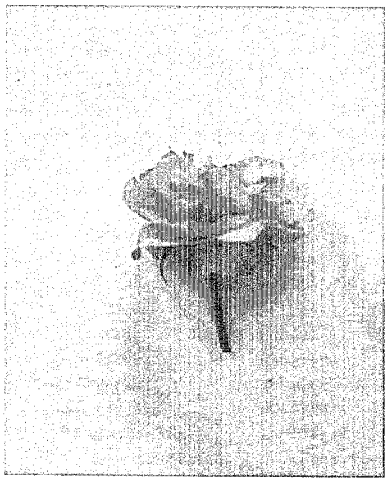
Figure 7:
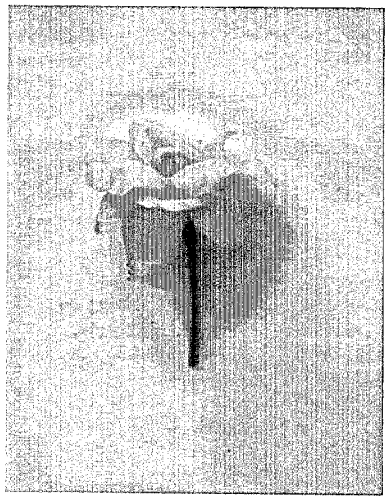
Figure 8:
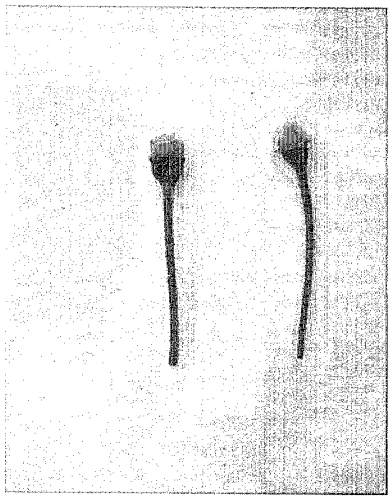
Figure 9:
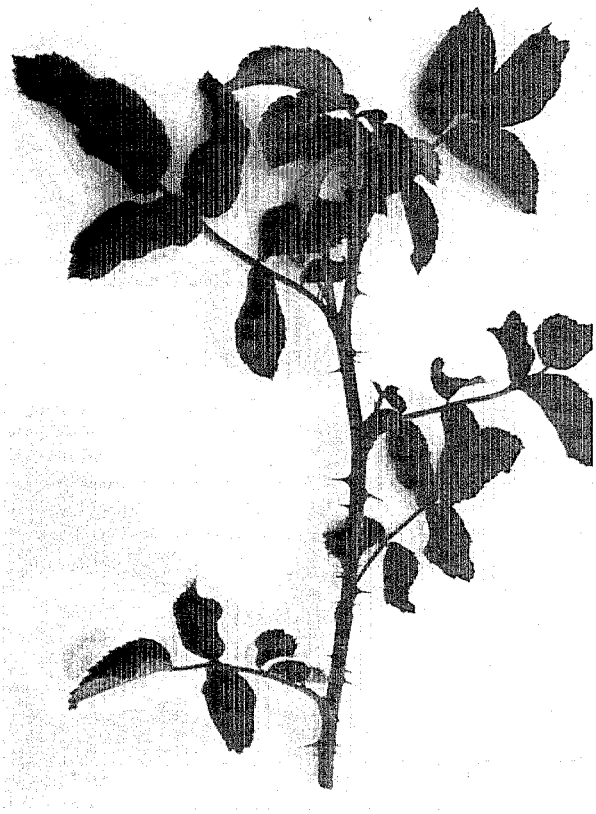
Figure 10:
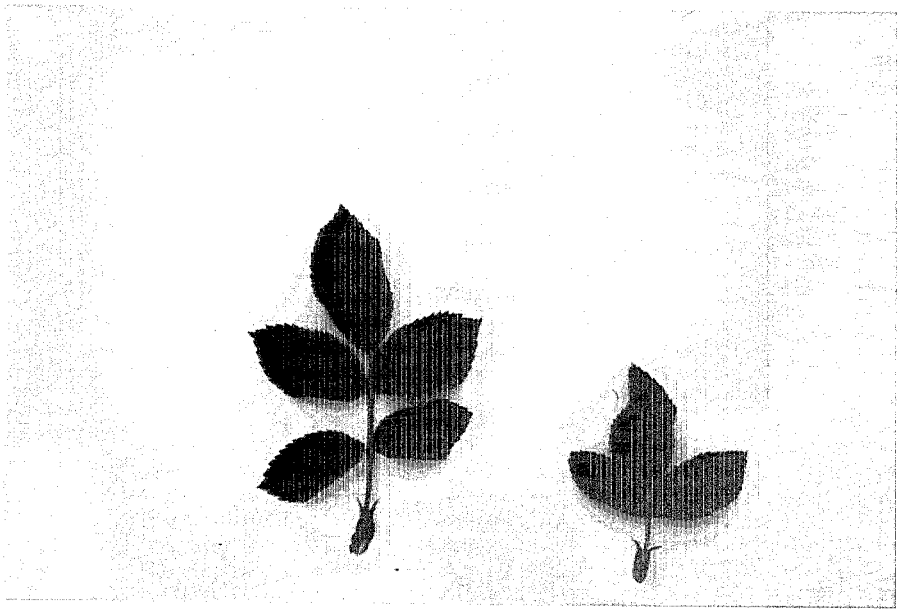
Figure 11:
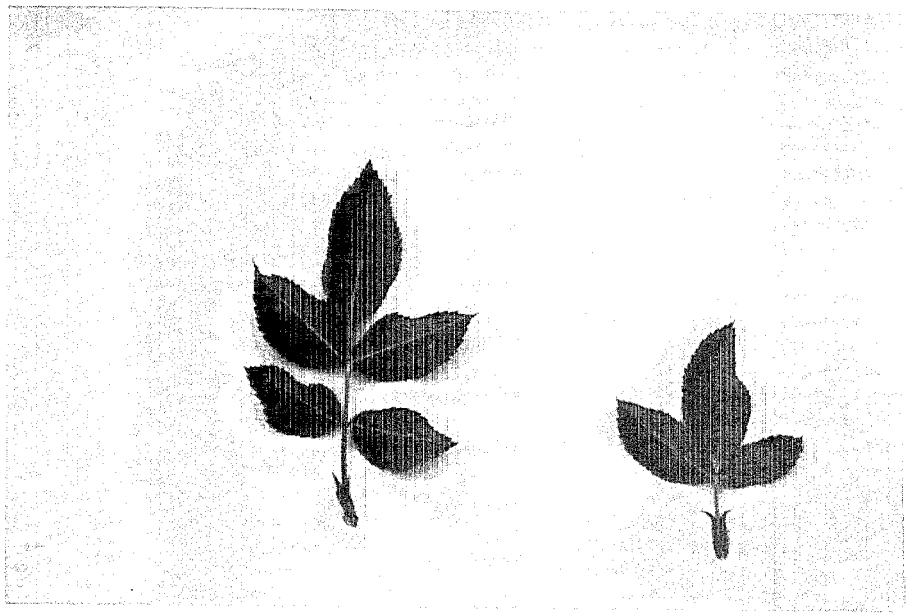

The chart used in the identification of colors is that of The Royal Horticultural Society (R.H.S. Colour Chart). Common color terms are to be accorded their ordinary dictionary significance. The description is based on the observation of 5 to 6 year-old plants of the new variety while being grown outdoors at L'Assomption, Quebec, Canada.

Class: Shrub.

Plant:

*Height.*—Approximately 0.6 meter on average.

*Width.*—Approximately 0.8 meter on average.

*Habit.*—Upright.

Branches:

*Color.*—Young stems: reddish. Mature stems: medium green.

*Prickles.*—Shape: slightly concave on the upper and under edges. Size: medium. Quantity: approximately 14 prickles per 100 mm of stem on average. Color: bright red when young and brown when mature.

Leaves: Compound and pinnate.

*Stipules.*—Narrow and erect.

*Petioles.*—Dark red when young and brownish green when mature.

*Petiolules.*—Very short.

*Leaflets.*—Number: commonly 3 or 5. Shape: oval base, some uneven, with acute tip. Serration: single and regular. General appearance: glossy. Rachis: smooth with very small prickles on the underside.

Color.—Dark green when young and yellow-green when mature.

Inflorescence:

*Number of flowers.*—Usually 1 to 4 per stem.

*Peduncle.*—Erect, commonly 4 to 4.5 cm. in length, bears very small prickles, red when young and green with red spotting when mature.

*Sepals.*—Commonly 5 in number, extend beyond the bud on young buds, commonly include foliation, green with red spotting when young and yellow green with red spotting when mature.

*Buds.*—Shape: ovoid before the opening of the sepals, and progressively becoming globular upon opening. Color upon opening: exhibit a blend of medium to pale pink.

*Flower.*—Shape: initially cup-shaped and subsequently assumes a flattened configuration (as illustrated). Diameter: approximately 5 cm on average. Color (when blooming): light pink, Red-Purple Group 58B, on upper surfaces, and light pink, Red-Purple Group 58C, on under surfaces. As the blossoms mature the coloration lightens as illustrated. Fragrance: slight. Petal number: commonly the flowers initially are single with approximately 5 petals, and commonly the subsequently formed flowers have up to approximately 22 petals. Petal texture: velvety. Lasting quality: the blossoms commonly last approximately 4 to 7 days while present on the plant under most growing conditions. Petal drop: the petals drop off fairly cleanly. Anthers: gold in coloration. Filaments: yellow-green in coloration. Pollen: light yellow in coloration. Receptacle: ovoid in configuration, green in coloration, and turning orange when fertile, with the formation of some hips.

Development:

*Vegetation.*—Intermediate vigor.

*Blossoming.*—Repeat flowering from June to October.

*Hardiness.*—Survives consistently without cover in Eastern Canada (Zone 4, Quellet and Sherk 1967).

*Resistance to diseases.*—Generally tolerant to blackspot, some mildew may be observed during damp growing conditions.

*Preferred mode of propagation.*—The use of softwood cuttings to produce self-rooted plants is recommended for the production of quality cold-tolerant plants.

I claim:

1. A new and distinct variety of shrub rose plant characterized by the following combination of characteristics:

(a) exhibits an upright growth habit with glossy foliage,
(b) forms in clusters attractive light pink blossoms that at least initially are single, propagates well by the use of softwood cuttings,
(d) exhibits a good winter hardiness, and
(e) is particularly well suited for growing in the landscape;

substantially as herein shown and described.

* * * * *